United States Patent [19]

Pigeon et al.

[11] 4,153,875
[45] May 8, 1979

[54] EDDY-CURRENT TESTING DEVICE FOR METAL TUBES WHICH ARE BENT AT LEAST LOCALLY

[75] Inventors: Michel Pigeon, Bures sur Yvette; Claude Vienot, Fontenay-sous-Bois, both of France

[73] Assignee: Commissariat a l'Energie Atomique, Paris, France

[21] Appl. No.: 709,946

[22] Filed: Jul. 29, 1976

[30] Foreign Application Priority Data

Aug. 7, 1975 [FR] France .............................. 75 24698

[51] Int. Cl.² ........................................... G01R 33/14
[52] U.S. Cl. .................................. 324/220; 324/228
[58] Field of Search ................ 324/37, 40, 228, 220; 33/178 F

[56] References Cited

U.S. PATENT DOCUMENTS

| | | | |
|---|---|---|---|
| 2,472,319 | 6/1949 | Turner | 324/37 |
| 3,474,541 | 10/1969 | Cubberly | 33/178 F |
| 3,483,466 | 12/1969 | Crouch et al. | 324/40 |
| 3,906,358 | 9/1975 | Stone | 324/37 |

*Primary Examiner*—M. Tokar
*Attorney, Agent, or Firm*—Cushman, Darby & Cushman

[57] ABSTRACT

The eddy-current testing device operates by translational motion of a probe within the interior of tubes to be tested. The probe comprises in succession from front to rear in its direction of normal translational motion a front guiding member, a coil-carrying member and a rear guiding member connected together by an elastic means which tends to maintain these three members in aligned relation. At least the coil-carrying member has maximum transverse dimensions which are smaller than the internal diameter of the tube. An emitter-receiver coil of the probe is connected electrically to an external supply and scanning system by means of a cable which is secured mechanically to the rear guiding member.

11 Claims, 3 Drawing Figures

EDDY-CURRENT TESTING DEVICE FOR METAL TUBES WHICH ARE BENT AT LEAST LOCALLY

This invention relates to an eddy-current testing device for metal tubes which are bent at least locally. The device operates by translational motion of a probe within the interior of said tubes, the probe being provided with an emitter-receiver coil and with an electric cable having conductors connected to said coil and coupled mechanically to the probe in order to accompany this latter in its translational motion while continuously emerging from the rear end of the tube in order to remain connected to a supply and scanning system located outside the tube.

Units which fall into the category of steam generators, condensers and heat exchangers are usually constituted by a bundle of metal tubes whose ends are assembled together on base plates. Current techniques call for the use of tubes having a complex geometry in which straight and curved portions follow in succession, namely tubes having hairpin bends, expansion bends, variable curvatures and coils. The tubes can be placed in several planes and their length can vary between 20 and 110 meters, especially in large steam generators, tubes of substantial length being obtained by means of the butt-welding process. The tubes of units of the above-mentioned type have an internal diameter which usually ranges from 8 to 25 mm and their radii of curvature can attain a value between 50 and 400 mm.

The dimensions, shape or interjacent arrangement of the tubes give rise to difficulties in regard to detection of flaws after these tubes have been assembled to form a bundle. Among the flaws encountered can be mentioned cracks, folds, corrosion of walls or of welds which are liable to result in incipient failure of tubes as well as to have unpredictable and undoubtedly very serious consequences both in regard to the unit considered and in regard to its environment. For example, in the tube of a heat exchanger in which water and sodium are circulated at the same time, defective leak-tightness produces a so-called wastage effect and this causes damage to the tubes in the vicinity of the leak location.

Methods of eddy-current testing are already known in which use is made of a probe having an emitter-receiver coil which travels within the interior of these tubes. It is known that these methods consist in studying variations in the eddy-currents produced within the tube to be examined by the alternating field of the coil. To this end, the coil through which a sinusoidal current passes produces an electromagnetic field which induces eddy currents within the tube. These currents produce on return an alternating field which is set up in opposition to the initial field and consequently modifies the impedance of the coil. The currents induced in the tube have the same frequency as the excitation current of the coil but have a different phase. Any discontinuity which is present within the tube at the level of the probe (change in transverse dimensions, variation of electrical conductivity, cracks and the like) modifies the path or the intensity of the eddy currents and consequently the impedance of the coil. The coil which is most commonly used is formed by two windings connected in opposition and placed on the two adjacent arms of a measuring bridge. The passage of a defect in the field of the coil results in unbalance of the bridge successively in both directions. The voltage obtained is scanned in phase and in amplitude.

However, when the tubes to be tested have small internal diameters with relatively substantial lengths and are bent at least locally, probes of the usual types do not prove wholly satisfactory, especially at the time of the passage of elbowed zones, ovalized zones or even overlaid zones.

The aim of the invention is to overcome these defects of known testing devices by producing a novel device which makes it possible among other things to ensure centering of the probe which lends itself to the configuration of the tube being scanned while maintaining suitable positioning of the part which carries the coil, a path of the probe which is adapted to the length of the longest tubes, a reduction in coefficients of friction between the probe and the internal wall of the tube, suppression of vibrations having the effect of producing parasitic signals which impair the accuracy of the measurement along the path.

To this end, the invention proposes an eddy-current testing device of the type defined in the foregoing introduction which is essentially characterized in that the probe comprises in succession from front to rear in its direction of normal translational motion a front guiding member, a coilcarrying member and a rear guiding member connected together by an elastic means which tends to align these three members of which at least the coil-carrying member has maximum transverse dimensions which are smaller than the internal diameter of the tube, the cable being connected mechanically to the rear guiding member. Preferably, the guiding members are adapted to carry on the external surface thereof antifriction devices (of the sliding or rolling type) which are intended to come into contact with the internal wall of the tube to be tested.

By means of this construction, the coil-carrying member is placed automatically in the axis of the rectilinear sections of the tubes to be tested. On the contrary, in the curved portions, said coil-carrying member is displaced offcenter towards the zone corresponding to the internal radius of curvature of the tube, that is, the zone which has acquired the greatest thickness at the time of bending of said tube, thus making it possible to test the tube throughout this thickness in spite of the "skin effect" which causes an exponential reduction of the eddy currents from the tube surface located nearest the probe, that is to say its internal surface.

In a first embodiment which applies preferably to the testing of tubes having a small internal diameter, the aforesaid elastic means is constituted by a helical spring around which are mounted the three members aforesaid at successive distances from each other. In this case, each guiding member can be formed of relatively resilient plastic material and can comprise a central tubular hub for applying the member considered against the helical spring, a disc whih projects radially at one of the ends of the hub and a series of fingers extending from said disc in the axial direction towards the other end of the hub and forming together at the free ends thereof a beaded edge which is radially deformable and constitutes one of the antifriction devices aforesaid. Accordingly and as a preferable feature, each guiding member comprises a second disc which projects radially at the other end of the hub, said other end being directed towards the front in the case of the front guiding member and towards the rear in the case of the rear guiding member. Said second disc has an external diameter which is smaller than that of the beaded edge and has a penetration profile (conical or the like) in the direction opposite to that of the first disc.

In addition to the three members aforementioned, the probe can comprise a fastening member for the electric cable, said fastening member being placed behind the rear guiding member and connected to this latter by a second elastic means such as a second helical spring. In order to facilitate extraction of the probe as a result of action on the electric cable in the event of failure of the first elastic means or helical spring, a traction element is advantageously secured at one end to the front guiding member and at the other end to the fastening member. In the event that both elastic means are constituted by helical springs, said traction element can be guided between the front guiding member and the fastening member as it passes inside said helical springs. In this case, it is an advantage to arrange the assembly so as to ensure that said helical springs normally maintain the traction element under slight tension. This makes it possible to secure said traction element to the front guiding member by means of an end-cap placed at the front of said member and maintained applied against this latter by virtue of the tension exerted on the traction element by the helical springs.

In a second embodiment, the elastic means for connecting together the front guiding member, the coil-carrying member and the rear guiding member is constituted by a series of elastic bellows elements.

In a third embodiment, the elastic means aforesaid is constituted by a mass of resilient plastic material in which the three members aforesaid are embedded.

The invention will now be explained in greater detail with reference to the accompanying drawings, wherein.

Figure 1:
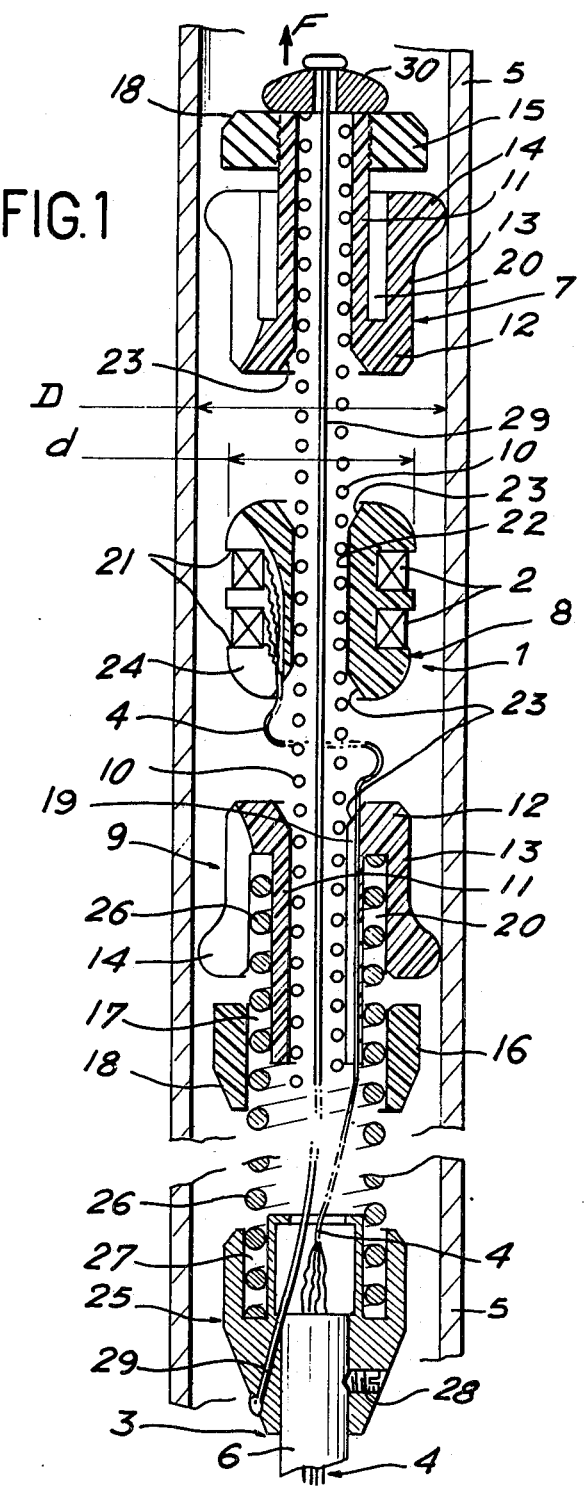
FIG. 1 is a longitudinal sectional view of a probe constructed in accordance with a first embodiment and placed within a rectilinear section of the tube to be tested.

The eddy-current testing device, the essential elements of which are shown diagrammatically in FIG. 1, operates by translational motion (in the direction of the arrow F) of a probe 1 fitted with an emitter-receiver coil 2 and comprises an electric cable 3. Said cable 3 has electric conductors 4 connected to said coil 2 and is attached to the probe 1 so as to accompany this latter in its translational motion while continuously emerging from the tube 5 to be tested through the rear end of this latter (the rear end being defined with respect to the direction F of translational motion) in order to remain connected to a supply and scanning system (not shown) located externally of the tube. There is combined with this system a device for exerting mechanical thrust (for example by means of pairs of pressure rollers driven in rotation) and if necessary for exerting pneumatic or hydraulic thrust which ensures translational motion of the probe 1 within the interior of the tube 5 at a speed which is preferably constant. The cable 3 also has a sheath 6 in which are contained or embedded the conductors 4 and which endows said cable with sufficient mechanical strength and in particular with resistance to buckling which enables this latter to transmit to the probe 1 the efforts exerted by the thrust device aforesaid irrespective of the depth of penetration of the probe 1 within the tube 5.

In accordance with the invention, the probe 1 comprises successively from the front to the rear in the direction of the arrow F a front guiding member 7, a member 8 for carrying the coil 2 and a rear guiding member 9. The three members 7, 8 and 9 are connected together by an elastic means 10 which tends to maintain them in aligned relation or in other words to place them in a straight line and the cable is connected mechanically (either directly or indirectly) to the rear guiding member 9.

In accordance with the embodiment of FIG. 1, the elastic means 10 is constituted by a metallic helical spring around which are mounted the members 7, 8, 9 at successive distances from each other.

Each of the two guiding members 7 and 9 is formed of relatively resilient plastic material and comprises : a central tubular hub 11 by means of which the member 7 or 9 is applied against the helical spring 10 ; a disc 12 which projects radially at one end of the hub 11 and a series of fingers 13 extending from said disc 12 in the axial direction towards the other end of the hub 11. By means of an outer bulge, said fingers 13 form together at the free ends thereof a beaded edge 14 which is radially deformable and constitutes an antifriction device which is intended to come into contact with the internal wall of the tube 5 to be tested.

Each of the two guiding members 7 and 9 further comprises a second disc 15 or 16 which projects radially at the other end of the hub 11, said other end being directed towards the front in the case of the front guiding member 7 and towards the rear in the case of the rear guiding member 9. As shown in FIG. 1, the second disc 15 of the front guiding member 7 can be attached directly to the hub 11, in particular by bonding. On the contrary, the second disc 16 of the rear guiding member 9 is mounted at a certain radial distance from the hub 11 so as to make provision for an annular space 17, the function of which will hereinafter become apparent. In both cases, the second disc 15 or 16 has an external diameter which is smaller than that of the beaded edge 14 and also smaller than the internal diameter of the tube 5 to be tested ; said second disc has a profile or surface of penetration 18 of conical shape, for example, in the direction F of translational motion in the case of the front guiding member 7 and in the opposite direction in the case of the rear guiding member 9.

It is therefore apparent that except for the discs 15 and 16, the guiding members 7 and 9 can be identical, with the result that the manufacture is more simple and more economical. At the time of assembly, it is nevertheless preferable in the case of the rear guiding member 9 to form a longitudinal groove 19 in its hub 11 in order that the conductors 4 can be more readily passed from the coil-carrying member 8 to the rear after they have been released from the sheath 6. Also noteworthy is the fact that an annular space 20 which is similar to the space 17 should be left free between the hub 11 and the fingers 13, said space 20 being employed only on the rear guiding member 9 as will hereinafter be described.

The coil-carrying member 8 is usually formed of the same material as the guiding members 7 and 9. Said member is provided externally with two channels 21 for receiving two windings connected in opposition which constitute the coil 2. The maximum external diameter d of said coilcarrying member is smaller than the internal diameter D of the tube 5 to be tested. The coil-carrying member 8 is provided internally with an axial passage 22 having a diameter which is equal to the internal diameter of the hubs 11 of the guiding members 7 and 9 in order to ensure that the helical spring 10 is capable by screwing or like means of engaging successively in the three members with elastic deformation such that said members are continuously maintained in the same longitudinal positions on the spring 10. In order to facilitate engagement of the spring, the members 7, 8 and 9 can be provided internally with flared entrances 23. The coil-carrying member 8 usually has a groove 24 which makes it possible for the conductors 4 to leave the coil 2 through the interior of the member 8.

In addition to the three members 7, 8 and 9, the probe 1 comprises a fastening member 25 for the electric cable 3 or more precisely for the sheath 6 of said cable. Said fastening member 25 is placed behind the rear guiding member 9 and is connected to this latter by a second elastic means. In the preferred embodiment shown in FIG. 1, said second elastic means is constituted by a helical spring 26 which passes with a certain degree of compression within the annular spaces 17 and 20 of the rear guiding member 9 and terminates within a channel 27 which is formed in the fastening member 25 and open towards the front. Said fastening member has a tubular shape in order to ensure that the front end of the cable 3 can pass through this latter axially. A locking screw 28 or like means serves to anchor the cable 3 to said member 25. The sheath 6 stops at the level of the front end of the fastening member 25; between this end and the coil-carrying member 8, the conductors 4 which are electrically and individually insulated are first taken back behind the rear guiding member 9 through the interior of the helical spring 26, then pass through said member 9 along the groove 19 externally of the helical spring 10 and finally penetrate into the coil-carrying member 8 via the groove 24. Along this path, the conductors 4 are given a certain amount of slack in order to permit bending of the probe without subjecting these leads to tensile stresses.

Finally, it may happen that the helical spring 10 which joins the members 7, 8 and 9 together breaks within the interior of the tube 5 to be tested. In that case, in order to facilitate extraction of the probe 1 by producing action on the electric cable 3, a traction element 29 such as a wire or metallic cable can be secured at one end to the front guiding member 7 and at the other end to the fastening member 25. Between the front guiding member 7 and the fastening member 25, the traction element 29 is guided as it passes inside the helical spring 10, then inside the helical spring 26. The complete assembly is so arranged that the springs 10, 26 normally maintain the traction element 29 under slight tension. This element 29 can accordingly be attached to the front guiding member 7 by means of an end-cap 30 placed on the front side of said member 7 and maintained applied against this latter by means of the tension to which the traction element 29 is subjected.

The operation of the testing instrument thus obtained will now be described. The probe 1 is introduced into the tube 5 and caused to advance within this latter by means of the thrust device aforementioned. The fluid (gas or liquid) which may be forced back by said device assists the forward displacement of the probe by reason of the pressure drop produced during transfer of the fluid by the baffle effect resulting from the probe. In the rectilinear sections of the tube, the three members 7, 8 and 9 are aligned by the helical spring 10 and the probe is centered by means of the beaded edges 14 which bear on the internal wall of the tube. In the curved sections of the tube, the coil-carrying member 8 comes closer to the wall corresponding to the internal radius of curvature of the tube as the value of said radius is lower. There thus comes a time when, in spite of the difference between the maximum external diameter d of the member 8 and the internal diameter D of the tube 5, the coil-carrying member 8 finally comes into contact with the tube, thus causing the spring 10 to bend in turn from this moment onwards. In any case, the coil 2 is displaced off-center towards that zone of the tube which has acquired the greatest thickness at the time of the tube bending operation, thus providing a highly favorable remedy to the "skin effect" mentioned earlier.

Once the test has been completed, the probe is withdrawn by applying traction to the electric cable 3. In both directions of the displacement, the surface 18 of penetration of the front guiding member 7 or of the rear guiding member 9 makes it possible for the probe 1 to pass over narrowed or overlaid zones. In the event of failure of the spring 10, all the probe components can readily be extracted by virtue of the presence of the traction element 29 and of the disc 15 which performs the function of a scraper and serves to recover the probe fragments resulting from either total or partial fracture of the probe. It should also be noted that the two springs 10 and 26 work under excellent conditions since they are banded at their extremities, one spring being banded by the hubs 11 and the other spring being banded by the disc 16 and the fastening member 25; in addition, the spring 10 is banded in the central portion thereof by means of the coil-carrying member 8. It is understood that the displacement of the probe can also be obtained by means of a liquid under pressure which is introduced into the tube to be tested behind said probe which produces action in particular on the beaded edges 14.

Figure 2:
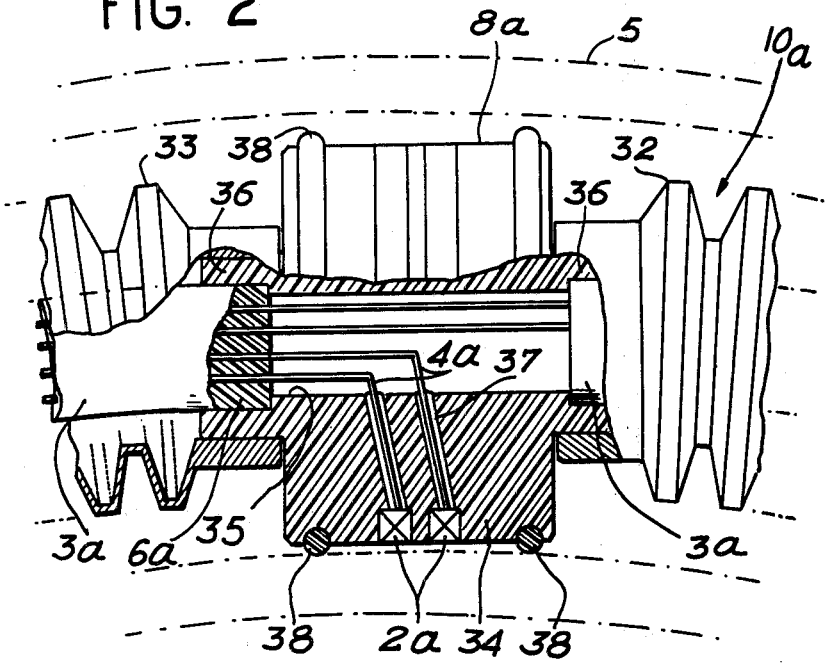
FIG. 2 is a longitudinal sectional view of a probe constructed in accordance with a second embodiment of the invention and placed within a curved section of the tube to be tested.

A second embodiment is illustrated in FIG. 2. In this embodiment, it has been endeavored to obtain a better penetration of the currents induced by the probe 1a by bringing the coils 2a as close as possible to the internal wall of the tube 5, said coils being accordingly mounted within a coil-carrying member 8a of a sliding type. Elements which are equivalent to those shown in the embodiment of FIG. 1 are designated in FIG. 2 by the same reference numerals followed by the letter a. The testing device of FIG. 2 therefore comprises, in addition to the probe 1a and the emitter-receiver coil 2a, a cable 3a having conductors 4a and a sheath 6a, a front guiding member 7 (not shown), a coilcarrying member 8a, a rear guiding member 9 (not shown), an elastic means 10a which tends to align the elements and members 7, 8a, 9. The rear guiding member 9 also serves as a fastening member for the cable 3a which is attached thereto by means of a screw or like means. As in the previous embodiment, the reference numeral 5 designates the tube to be tested and the reference F designates its direction of normal translational motion. In this embodiment, the elastic means 10a is no longer constituted by a helical spring but by a set of bellows elements 32 and 33 formed of elastic material and anchored to the element and members 7, 8a, 9 in such a manner as to tend to bring these latter into aligned relation. These bellows elements establish connections and articulations such as to attenuate the transmission of mechanical vibrations to the coils 2a.

The coil-carrying member 8a comprises a cylindrical body 34 of insulating material pierced by an axial passage 35 and has two bearing surfaces or spigot ends 36 for connecting the bellows elements 32 and 33. The coils 2a are contained within rectangular annular channels formed in the lateral surface of the body 34. The conductors 4a extend to the coils 2a through radial passages 37 and these latter open into the passage 35 which is the point of arrival of said conductors 4a. The passage 35 is sealed by means of a flexible resin after the connections have been made. Elastic rings 38 are placed at the ends of the body 34 with a view on the one hand to facilitating sliding motion within the interior of the tube 5 and on the other hand to increasing the pressure drop of the thrust fluid.

The front guiding member 7 can be formed by a head carriage and by an intermediate carriage. A bellows element serves to connect the two carriages.

Figure 3:
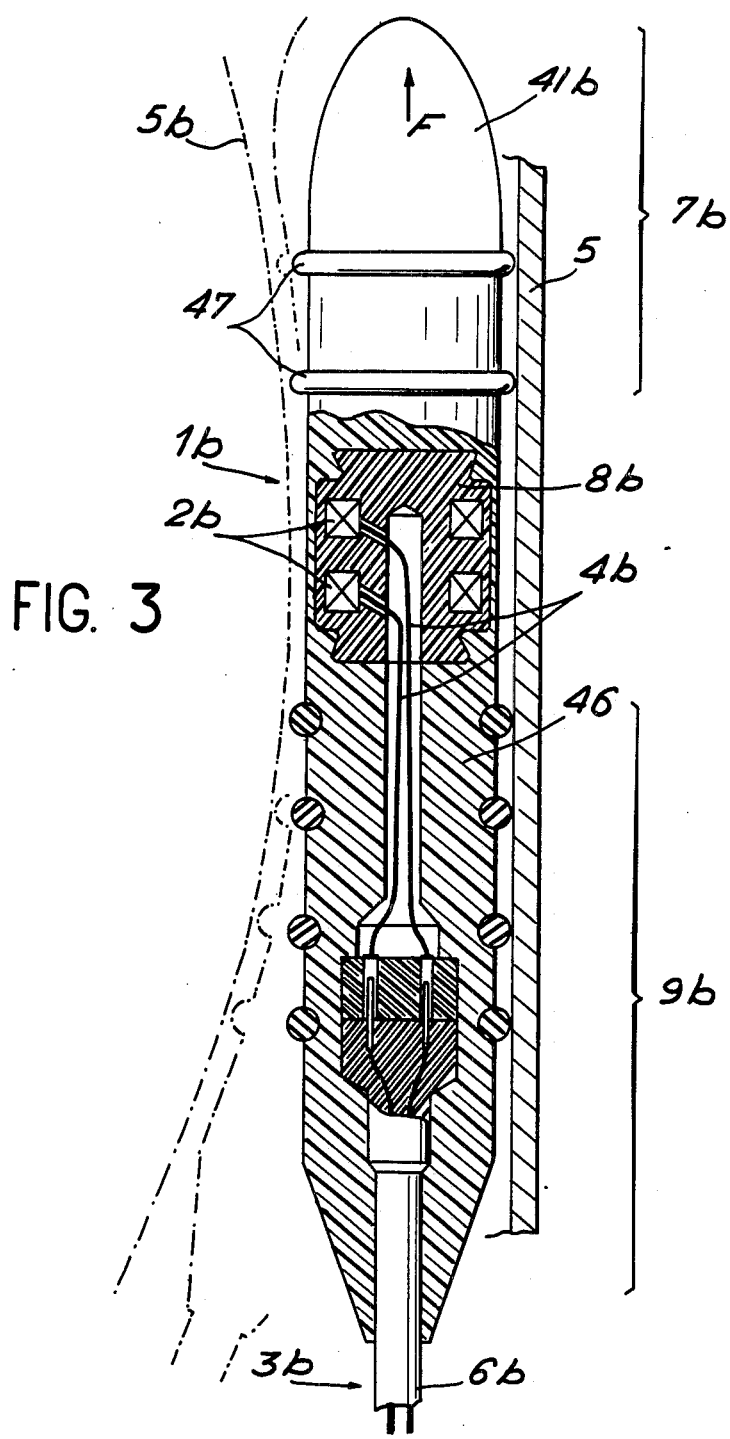
FIG. 3 is a longitudinal sectional view of a probe constructed in accordance with a third embodiment of the invention and placed within a rectilinear section of the tube to be tested and shows the deformation of said probe as this latter passes within elbowed sections of said tube.

A third embodiment is shown in FIG. 3. In this embodiment, it has been sought to make the probe 1b easier to control. The elements which are equivalent to those shown in the embodiment of FIG. 1 are designated in FIG. 3 by the same reference numerals followed by the letter b. The control device of FIG. 3 therefore comprises in addition to the probe 1b, an emitter-receiver coil 2b, a cable 3b having conductors 4b and a sheath 6b, a front guiding member 7b, a coil-carrying member 8b and a rear guiding member 9b. In this embodiment, the elastic means for interconnecting the members 7b, 8b and 9b is constituted by a mass of resilient plastic material 46 in which these three elements are embedded. In that portion which constitutes the front guiding element 7b, the mass 46 has a bullet nose 41b. In those portions which constitute the front guiding element 7b and rear guiding element 9b, the mass 46 is surrounded by metallic rings 47 which form an antifriction element. As shown in FIG. 3, the rear guiding element 9b serves as a fastening member for the cable 3b.

There is shown in full lines in FIG. 3 the rectilinear shape assumed by the probe 1b in a rectilinear section of the tube 5 to be tested, a rectilinear section of this type being in turn shown in full lines on the right-hand side of FIG. 3. On the left-hand side of this figure, there is shown in chain-dotted lines the contour of a curved tube 5b and the curved shape assumed by the probe 1b as a result of elastic deformation of the mass 46. This embodiment makes it possible to control the probe in a simple manner since its various elements are grouped together within the mass 46.

What we claim is:

1. An eddy-current testing device for metal tubes bent at least locally so that an inner radius of curvature has a greater thickness than the outer radius of curvature and having a given internal diameter, said device operating by translational motion of a probe within the interior of said tubes, the probe being provided with an emitter-receiver coil and with an electric cable having conductors connected to said coil and coupled mechanically to the probe in such a manner as to accompany said probe in its translational motion while continuously emerging from the rear end of the tube in order to remain connected to a supply and scanning system located outside said tube, wherein the probe comprises successively from front to rear in the direction of normal translational motion thereof a front guiding member, a coil-carrying member and a rear guiding member, said front and rear guiding members having an outer diameter substantially equal to said internal diameter, and elastic means, said members being connected together by said elastic means which tends to align said three members, said coil carrying member having maximum transverse dimensions which are so much smaller than said given internal diameter and said front and rear guiding members being so spaced from said coil-carrying member, that in movement around curved portions of said tube the coil-carrying member is displaced toward the inner radius of curvature of the portion and the impedance of said coil remains substantially constant, the cable being connected mechanically to the rear guiding member.

2. A testing device according to claim 1, wherein the guiding members carry on the external surface thereof anti-friction devices for contacting the internal wall of the tube to be tested.

3. A testing device according to claim 1, wherein the elastic means is constituted by a helical spring around which are mounted the three members aforesaid at successive distances from each other.

4. A testing device according to claim 2, wherein said elastic means includes a helical spring and each guiding member is formed of relatively resilient plastic material and comprises a central tubular hub for applying the member against the helical spring, a disc which projects radially at one of the ends of the hub and a series of fingers extending from said disc in the axial direction towards the other end of the hub and forming together at the free ends thereof a beaded edge which is radially deformable and constitutes one of the antifriction devices aforesaid.

5. A testing device according to claim 4, wherein each guiding member comprises a second disc which projects radially at the other end of the hub, said other end being directed towards the front in the case of the front guiding member and towards the rear in the case of the rear guiding member, the external diameter of said second disc being smaller than that of the beaded edge and having a penetration profile in a direction opposite to that of the first disc.

6. A testing device according to claim 5, wherein the probe comprises a fastening member for the electric cable, said fastening member being placed behind the rear guiding member and connected thereto by a second elastic means comprising a second helical spring.

7. A testing device according to claim 6, wherein a traction element is secured at one end to the front guiding member and at the other end to the fastening member.

8. A testing device according to claim 7, wherein the traction element is guided between the front guiding member and the fastening member as it passes inside said helical springs.

9. A testing device according to claim 8, wherein the helical springs normally maintain the traction element under slight tension.

10. A testing device according to claim 1, wherein the elastic means for connecting together the front guiding member, the coil-carrying member and the rear guiding member is constituted by a series of elastic bellows elements.

11. A testing device according to claim 1, wherein the elastic means for connecting together the front guiding member, the coil-carrying member and the rear guiding member is constituted by a mass of resilient plastic material in which the three members aforesaid are embedded.

* * * * *